(12) United States Patent

Watanabe et al.

(10) Patent No.: US 7,060,803 B2
(45) Date of Patent: Jun. 13, 2006

(54) METAL COMPLEX-PROTEIN COMPOSITE AND HYDROGENATION CATALYST

(75) Inventors: Yoshihito Watanabe, Aichi-ken (JP); Takafumi Ueno, Aichi-ken (JP); Satoshi Abe, Aichi-ken (JP)

(73) Assignee: Nagoya Industrial Science Research Institute, Nagoya (JP)

( * ) Notice: Subject to any disclaimer, the term of this patent is extended or adjusted under 35 U.S.C. 154(b) by 163 days.

(21) Appl. No.: 10/790,060

(22) Filed: Mar. 2, 2004

(65) Prior Publication Data

US 2005/0049405 A1   Mar. 3, 2005

(30) Foreign Application Priority Data

Sep. 2, 2003   (JP) .............................. 2003-310085

(51) Int. Cl.
 C07K 1/32 (2006.01)
 C07C 29/158 (2006.01)
(52) U.S. Cl. ................... 530/391.3; 530/400; 530/223; 530/389.6; 514/2; 514/6
(58) Field of Classification Search ............. 530/391.3, 530/400, 223, 389.6; 514/2, 6
 See application file for complete search history.

(56) References Cited

OTHER PUBLICATIONS

Yu et al. (1999) Disordered water within a hydrophobic protein cavity visualized by x-ray crystallography. Proc. Natl. Acad. Sci. U S A. vol. 96, No. 1, pp. 103-108.*
NCBI Sequence Viewer (2005) CAA48412, muoglobin amino acid sequence, http://www.nci.nlm.nih.gov/entrez/viewer.fcgi?db=protein&val=10120.*
NCBI Sequence Viewer (2005) NP 776306, muoglobin amino acid sequence, http://www.nci.nlm.nih.gov/entrez/viewer.fcgi?db=protein&val=27806939.*
Zhu et al. (1994) Site-specific hydrolytic. cleavage of cytochrome c and of its heme undecapeptide, promoted by coordination complexes of palladium(II), J. Am. Chan. Soc. vol. 116, pp. 5218-5224.*
Cadierno et al. (May 2003) Ruthenium(II) and ruthenium(IV) complexes containing kappa1-P-, kappa2-P,O-, and kappa3-P,N,O-iminophosphorane-phosphine ligands Ph2PCH2P[=NP(=O)(OR)2]Ph2 (R = Et, Ph): synthesis, reactivity, theoretical studies, and catalytic activity in transfer hydrogenation of cyclohexanone. Inorg. Chem. vol. 42, No. 10, pp. 3293-3307.*

(Continued)

*Primary Examiner*—Jon Weber
*Assistant Examiner*—Samuel Wei Liu
(74) *Attorney, Agent, or Firm*—Oliff & Berridge, PLC

(57) ABSTRACT

A metal complex-protein composite comprising apohemoglobin, apoheme oxygenase, apocatalase or apoferrin having cavity and a metal complex has a specific structure that the metal complex is received in the cavity of the apoprotein. The metal complex is prepared by complexation of a metal ion, which is selected from the group consisting of rhodium, ruthenium, and palladium, with a ligand. The metal complex-protein composite functions as a hydrogenation catalyst of an olefin in water. The metal complex-protein composite is thus effectively applied to hydrogenation of water-soluble subtrates and has enviromental advantages over organic solvents.

8 Claims, 2 Drawing Sheets

OTHER PUBLICATIONS

Smolenski et al. (Mar. 2003) New rhodium(III) and ruthenium(II) water-soluble complexes with 3,5-diaza-1-methyl-1-azonia-7-phosphatricyclo[3.3.1.1(3,7)]decane. Inorg. Chem. vol. 42, No. 10, pp. 3318-3322.*

Witting et al. (2001) Reaction of human myoglobin and H2O2. Electron transfer between tyrosine 103 phenoxyl radical and cysteine 110 yields a protein-thiyl radical. J. Biol. Chem. vol. 276, No. 19, pp. 16540-16547.*

Wagner et al. (1995) Structure determination of the biliverdin apomyoglobin complex: crystal structure analysis of two crystal forms at 1.4 and 1.5 Angstroms resolution. J. Mol. Biol. vol. 247, No. 2, pp. 326-337.*

Jackson et al. (2000) placement of Ru(bpy)2 in the heme pocket of cytochrome B5, Book of Abstract, 219th ACS National Meeting, San Francisco, CA, Mar. 26-30, 2000, Abstract No. 510.*

Ohde et al. (2002) Hydrogenation of olefins in supercritical CO(2) catalyzed by palladium nanoparticles in a water-in-CO(2) microemulsion. J. Am. Chem. Soc. vol. 124, No. 17, pp. 4540-4541.*

M. Ohashi et al. "Abstracts of Symposium on Biofunctional Chemistry," Chiba University, Sep. 20-21, 2001. (w/ translation).

J. M. Brown et al. "The Mechanism of Asymmetric Homogeneous Hydrogenation. Solvent Complexes and Dihydrides from Rhodium Diphosphine Precursors," Journal of Organometallic Chemistry, vol. 216, 1981, pp. 263-276.

T. Matsui et al. "Formation and Catalytic Roles of Compound I in the Hydrogen Peroxide-Dependent Oxidations by HIS64 Myoglobin Mutants," J. Am. Chem. Soc., vol. 121, 1999, pp. 9952-9957.

F. Ascoli et al. "Preparation and Properties of Apohemoglobin and Reconstituted Hemoglobins," Methods in Enzymology, vol. 76, 1981, pp. 72-87.

R. Baughn et al. "Conversion of a Protein to a Homogeneous Asymmetric Hydrogenation Catalyst by Site-Specific Modification with a Diphosphinerhodium(I) Moiety," Journal of the American Chemical Society, 100:1, Jan. 4, 1978, pp. 306-307.

J. Collot et al. "Artificial Metalloenzymes for Enantioselective Catalysis Based on Biotin-Avidin," J. Am. Chem. Soc., vol. 125, 2003, pp. 9030-9031.

* cited by examiner

Rhodium Complex-Apomyoglobin Composite

| Examples | Apomyoglobin | J in Rhodium Complex | Observed Value by MS (Calculated Value) |
|---|---|---|---|
| 3 | apo−H64A Mb | $(CH_2)_2$ | 17764.8 (17765.4) |
| 4 | apo−Mb | $(CH_2)_2$ | 17829.9 (17831.1) |
| 5 | apo−Mb | $(CH_2)_4$ | 17859.8 (17859.2) |
| 6 | apo−H64D Mb | $(CH_2)_2$ | 17808.0 (17809.1) |

METAL COMPLEX-PROTEIN COMPOSITE AND HYDROGENATION CATALYST

BACKGROUND OF THE INVENTION

1. Field of the Invention

The present invention relates to a novel metal complex-protein composite and a novel hydrogenation catalyst.

2. Description of the Prior Art

This application claims foreign benefit of the filing date under 35 U.S.C. 119 of Japan application 2003-310085, filed Sep. 2, 2003.

The inventor of the present invention has proposed metal complex-protein composites of manganese-Schiff base complexes inserted in a cavity of apomyoglobin (apo-Mb) by non-covalent bonding. Here apomyoglobin is obtained by liberating a heme from an oxygen storage protein, myoglobin (Mb). The inventor synthesized, for example, a metal complex-protein composite including a metal complex of manganese with N,N'-bis(salicylidene)-1,2-phenylenediamine kept in the cavity of apomyoglobin, and reported that such composites were useful for asymmetric oxidation reaction of thioanisole (the Proceedings of the 16$^{th}$ Biofunctional Symposium, '1S1-11 Construction of Artificial Enzyme by Insertion of Metal Complex into Apomyoglobin Cavity' (published in September 2001).

The study of these metal complex-protein composites has just started, and no useful metal complex-protein composites for hydrogenation reaction have been reported so far.

SUMMARY OF THE INVENTION

The object of the invention is thus to provide a novel metal complex-protein composite. The object of the invention is also to provide a novel hydrogenation catalyst.

The inventor of this invention has developed a novel metal complex-protein composite as a fruit of intensive studies. The metal complex-protein composite of the present invention includes a protein having a cavity and a metal complex and has a specific structure that the metal complex is received in the cavity of the protein. Here the metal complex is prepared by complexation of a metal ion, which is selected among the group consisting of rhodium, ruthenium, and palladium, with a ligand. The metal complex-protein composite of the invention functions as a hydrogenation catalyst of an olefin in water. The metal complex-protein composite is thus effectively applied to hydrogenation of water-soluble substrates and has environmental advantages over organic solvents.

Any of diverse methods may be applied to synthesis of the metal complex-protein composite of the invention. Typically there are two applicable methods. One method inserts the metal complex into the cavity of the protein. The other method adds a material of the metal complex (the material that is changed to the metal complex by a reaction), which is to be received in the cavity of the protein, to a system including the protein having the cavity and synthesizes the metal complex in the system simultaneously with insertion of the metal complex into the cavity. One concrete procedure of the former method mixes the protein having the cavity with the metal complex at an equivalent ratio of 1 to 0.5 through 100 or preferably at an equivalent ratio of 1 to 1.1 through 2. Preferable solvents for the mixing reaction include mixed solvents of water and acetone, mixed solvents of water and methanol, mixed solvents of water and dimethylformamide (DMF), mixed solvents of water and dimethyl sulfoxide (DMSO), and water alone. Especially preferable are mixed solvents of water and acetone and mixed solvents of water and methanol. The mixing temperature is in a range of −10 to 200° C. and is preferably in a range of 1 to 4° C. The mixing time is in a range of 0.5 minutes to 24 hours and preferably in a range of 5 to 30 minutes. One concrete procedure of the latter method mixes the protein with the metal ion at an equivalent ratio of 1 to 0.5 through 100 or preferably at an equivalent ratio of 1 to 1.1 through 2. Preferable solvents for the mixing reaction include mixed solvents of water and acetone, mixed solvents of water and methanol, mixed solvents of water and DMF, mixed solvents of water and DMSO, and water alone. Especially preferable are mixed solvents of water and acetone and mixed solvents of water and methanol. The mixing temperature is in a range of −10 to 200° C. and is preferably in a range of 1 to 4° C. The mixing time is in a range of 0.5 minutes to 24 hours and preferably in a range of 5 minutes to 1 hour. Another applicable procedure inserts the metal complex into the cavity of the protein carried on a carrier by either of the above two methods. Still another applicable procedure prepares a metal complex-protein composite and replaces the ligand of the metal complex with another ligand.

The protein of the invention may be any one of proteins having either of an amino acid residue that coordinates to the selected metal ion of the metal complex and an amino acid residue that forms a non-covalent bond to the ligand of the metal complex in the cavity thereof, multimers of such proteins, and variants of such proteins. The protein of the invention may otherwise be any one of proteins having the cavity in a heme site by removing a heme from heme-containing proteins, multimers of such proteins, and variants of such proteins. Concrete examples include apomyoglobin, apohemoglobin, apoheme oxygenase, apocatalase, apocytochrome, apoferritin, and their variants. The terminology 'apo' is a prefix representing a protein having a defective cofactor or a defective prosthetic group. Apomyoglobin and apohemoglobin have a defective heme, and apoferritin has a defective iron ion. The variant of the protein preferably has a replacement of an amino acid residue at a position affecting the chemical reaction field of the metal complex received in the cavity of the protein with another amino acid residue suitable for the chemical reaction. The variant of apomyoglobin is, for example, apomyoglobin (a polypeptide chain of 153 amino acids) having a replacement of one or more of the 64$^{th}$ amino acid residue, the 71$^{st}$ amino acid residue, the 93$^{rd}$ amino acid residue, and the 107$^{th}$ amino acid residue. Especially preferable is an apomyoglobin variant having a replacement of the 64$^{th}$ histidine (His64) with an amino acid residue smaller than histidine, such as glycine or alanine.

The metal complex of the invention may be any metal complex of the metal ion coordinating to an amino acid residue located in the cavity of the protein or any metal complex of the ligand forming a non-covalent bond to the amino acid residue located in the cavity of the protein. A metal complex including a compound having a phosphino group as the ligand is preferable. Especially preferable is a metal complex including a compound having at least two diphenylphosphino groups as the ligand. One example of the preferable ligand is given as Formula (1):

$$R^1R^2P-J-PR^3R^4 \quad (1)$$

where $R^1$ through $R^4$ represent any of completely identical, partially identical, and completely different substituted and non-substituted hydrocarbons of 1 to 10 carbon atoms and substituted and non-substituted phenyls, and J represents any of substituted and non-substituted hydrocarbons of 1 to 10 carbon atoms and two carbon atoms included in benzene rings.

The phosphino ligand is not specifically restricted, but may be, for example, any of bis(diphenylphosphino)methane, bis(diphenylphosphino)ethane, bis(diphenylphosphino)propane, bis(diphenylphosphino)butane, bis(diphenylphosphino)pentane, bis(diphenylphosphino)hexane, 1,2-bis(diphenylphosphino)benzene, bis(dimethylphosphino)methane, bis(dimethylphosphino)ethane, bis(dimethylphosphino)propane, bis(dimethylphosphino)butane, bis(dimethylphosphino)pentane, bis(dimethylphosphino)hexane, 1,2-bis(dimethylphosphino)benzene, and bis(diphenylphosphino) compounds having one or more hydrogen atoms in the phenyl group displaced by any of substituent groups including alkyl groups, alkoxy groups, nitro groups, carboxyl groups, and halogens. These phosphino ligands are preferably used for the ligand of rhodium complexes and palladium complexes.

The ligand is not restricted to the phosphino ligand but may be a cyclic diene or an aromatic compound that reacts with a metal to produce a metallocene compound. Typical examples of the cyclic diene include cyclopentadiene, cyclooctadiene, and cyclopentadiene and cyclooctadiene derivatives having one or more hydrogen atoms displaced by any of substituent groups including alkyl groups, alkoxy groups, nitro groups, carboxyl groups, and halogens. Typical examples of the aromatic compound include benzene, naphthalene, and benzene and naphthalene derivatives having one or more hydrogen atoms displaced by any of substituent groups including alkyl groups, alkoxy groups, nitro groups, and carboxyl groups, for example, toluene, xylene, isopropyl benzene, isobutyl benzene, o-, m-, and p-isopropyltoluene (cymene), and o-, m-, and p-isobutyltoluene. These ligands are preferably used for the ligand of ruthenium complexes.

The hydrogenation catalyst of the invention is composed of the metal complex-protein composite discussed above and functions to accelerate hydrogenation in water. The amount of the hydrogenation catalyst used depends upon the reaction vessel and the economical efficiency. The molar ratio S/C (where S denotes a reaction substrate and C denotes the catalyst) is preferably in a range of 10 to 10000 or more specifically in a range of 50 to 5000. The reaction substrate is not specifically restricted but may be any compound having a site to be hydrogenated. The reaction substrate is preferably water-soluble, since hydrogenation takes place in water. Any aqueous solvent may be used for the solvent of the hydrogenation reaction. Typical examples include water, mixed solvents of water and lower alcohols (for example, methanol and ethanol), mixed solvents of water and lower ketones (for example, acetone and methyl ethyl ketone), mixed solvents of water and DMF, and mixed solvents of water and DMSO. The reaction temperature is in a range of −10 to 200° C. and is preferably in a range of 1 to 50° C. The mixing time is in a range of 0.5 minutes to 24 hours and is preferably in a range of 5 minutes to 10 hours. This hydrogenation reaction may be in a batchwise operation or in a flow operation.

EXAMPLES

Some examples of the invention are discussed below. In the description below, 'cod', 'dppe', and 'dppb' respectively represent 1,5-cyclooctadiene, 1,2-bis(diphenylphosphino)ethane, and 1,4-bis(diphenylphosphino)butane.

Example 1

Synthesis of Rhodium Complex 1

Rh(I)(cod)(dppe) was synthesized according to the procedure disclosed in a cited reference (Brown, J. M. et al., Journal of Organometallic Chemistry, 1981, vol216, p263–276). The procedure of synthesis mixed $[Rh(cod)Cl]_2$ (99 mg, 0.2 mmol) with $AgBF_4$ (80 mg, 0.41 mmol) in acetone in an atmosphere of argon with stirring for three hours and added solid dppe (159 mg, 0.4 mmol) to yield a red solution. The procedure concentrated the red supernatant to 3 ml and added ether (20 ml) to the concentrate to yield a yellow precipitate. The yellow precipitate was washed with ether and was evaporated. This gave an object compound, Rh(I)(cod)(dppe).BF4. The observed values by ESI-TOF MS (electrospray ionization time-of-flight mass spectrometry) were $[Rh(I)(cod)(dppe)]^+$m/z: 609.10 (calculated value: 609.14), $[Rh(I)(dppe)(CH_3OH)]^+$m/z: 533.03 (calculated value: 533.38), and $[Rh(dppe)]^+$m/z] 501.02 (calculated value: 501.04).

Example 2

Synthesis of Rhodium Complex 2

Rh(I)(cod)(dppb) was purchased from Sigma-Aldrich Inc. The product name was [1,4-bis(diphenylphosphino)butane](1,5-cyclooctadiene)rhodium tetrafluoroborate.

Example 3

Figure 1:
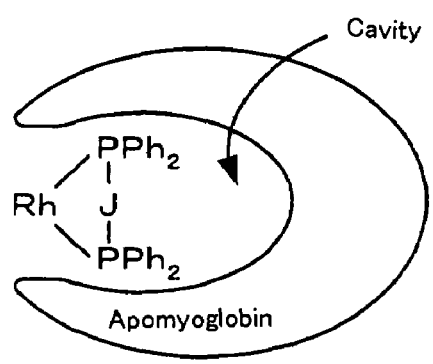
FIG. 1 shows Examples 3 through 6.
Figure 2:
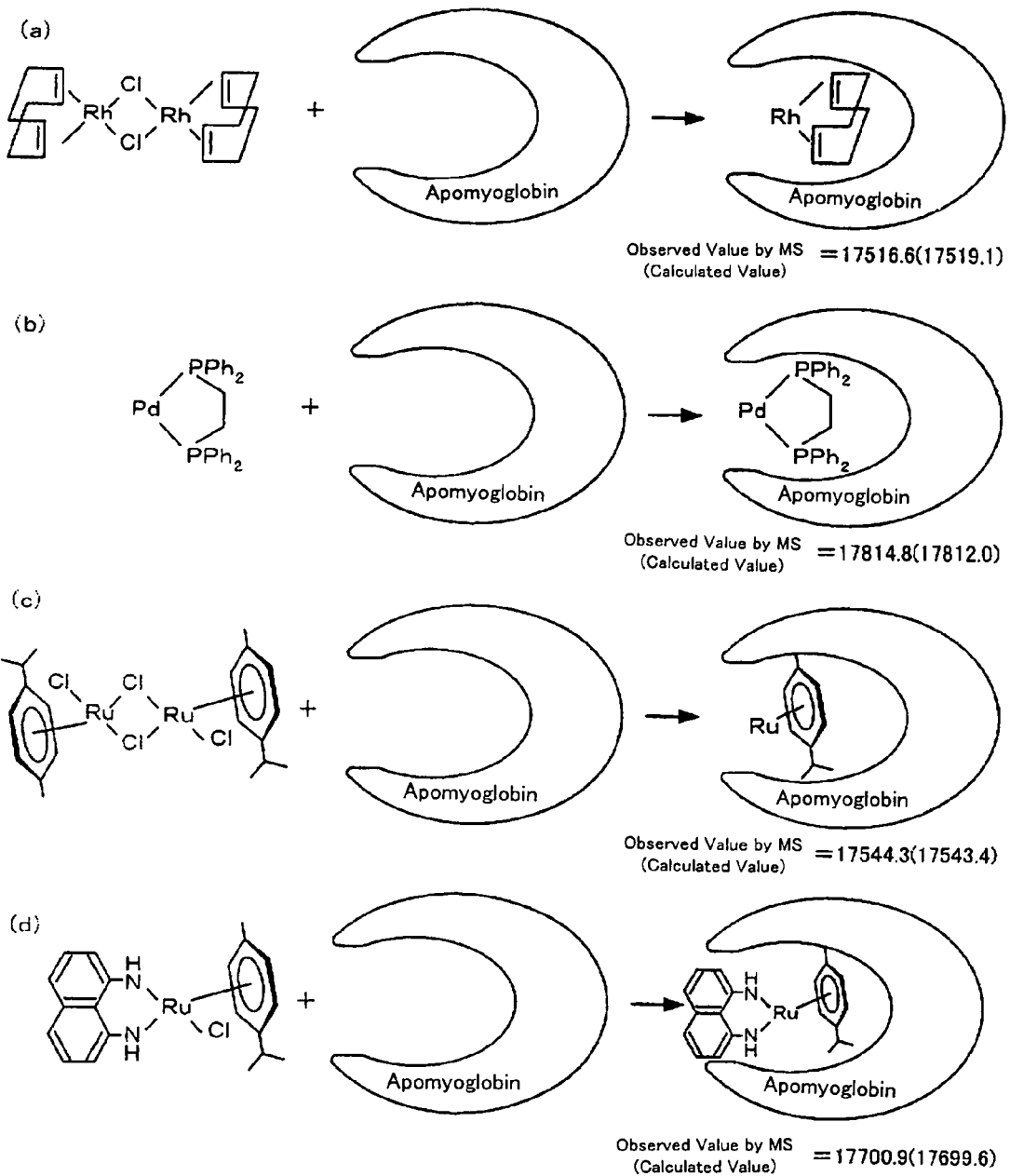
FIGS. 2(a)–(d) show syntheses of various metal complex-protein composites.

Synthesis of Rhodium Complex-Apomyoglobin Composite 1 (see FIG. 1)

All the operations for the synthesis were performed at a temperature of 4° C. Histidine as the $64^{th}$ amino acid residue of myoglobin was replaced with alanine according to the procedure disclosed in a cited reference (T. Matsui et al. J. Am. Chem. Soc., 1999, vol121, p9952–9957). The variant myoglobin is hereafter referred to as SW H64A Mb. The variant myoglobin SW H64A Mb was processed by the acid-butanone method described in a cited reference (F. Ascole et al. Method Enzymol. 1981, vol76, p72–87) and was successively dialyzed with 1 mM, 5 mM, and 10 mM Tris/HCl buffer solutions (pH 7.0) for 2 hours each. This gave apomyoglobin, which is hereafter referred to as apo-H64A Mb. The procedure then mixed apo-H64A Mb with 10 mM Tris/HCl buffer solution (pH 7.0) (385 μM, 18 ml), added the acetone solution of the rhodium complex (10 mM, 1.038 ml) obtained in Example 1 with stirring to an equivalent ratio of 1.5 Rh to 1 Mb, and stood still at 4° C. for 10 minutes. The resulting mixed solution was dialyzed overnight with 1 liter of 10 mM Bis Tris/HCl buffer solution (pH 6.0). The reconstructed rhodium complex-apomyoglobin composite Rh(dppe)-apo-H64A Mb was purified by gel filtration with G25 and G50 (10 mM Tris/HCl buffer solution (pH7.0)). Here G25 and G50 respectively represent Sephadex G25 Medium and Sephadex G50 Medium (manufactured by Amersham Biosciences K.K.). The resulting composite was identified by ESI-TOF MS, UV-vis analysis, and atomic absorption spectroscopy. The observed value by ESI-TOF MS was 17764.8, which well agreed with the calculated value 17765.4. The absorption maximum wavelength of the composite in UV-vis (ultraviolet-visible spectroscopy) was 259.5 nm, which was lower than the absorption maximum wavelength of apo-H64A Mb (280 nm). The concentration of Rh was determined to be 1.77 mM by atomic absorption spectroscopy.

Example 4

Synthesis of Rhodium Complex-Apomyoglobin Composite 2 (see FIG. 1)

A rhodium complex-apomyoglobin composite Rh(dppe).apo-Mb was obtained according to the same procedure as that of Example 3, except that myoglobin was not replaced. The observed value of the resulting composite by ESI-TOF MS was 17829.9, which well agreed with the calculated value 17831.1. The absorption maximum wavelength of the composite in UV-vis analysis was 274.5 nm, which was lower than the absorption maximum wavelength of apo-Mb (280 nm). The concentration of Rh was determined to be 1.13 mM by atomic absorption spectroscopy.

Example 5

Synthesis of Rhodium Complex-Apomyoglobin Composite 3 (see FIG. 1)

A rhodium complex-apomyoglobin composite Rh(dppb).apo-Mb was obtained according to the same procedure as that of Example 4, except that the rhodium complex obtained in Example 2 was used instead of the rhodium complex obtained in Example 1. The observed value of the resulting composite by ESI-TOF MS was 17859.8, which well agreed with the calculated value 17859.2.

Example 6

Synthesis of Rhodium Complex-Apomyoglobin Composite 4 (see FIG. 1)

Another method was applied to synthesize a rhodium complex-apomyoglobin composite. This method synthesizes a rhodium complex in situ in the presence of apomyoglobin to obtain the rhodium complex-apomyoglobin composite. The procedure added an acetone solution of [Rh(cod)Cl]$_2$ (2 mM, 2 µl) (at an equivalent ratio of 2 Rh to 1 Mb) and an acetone solution of dppe (2 mM, 4 µl) to a 5 mM ammonium acetate solution of apo-H64D Mb (having a replacement of a 64$^{th}$ histidine with aspartic acid) (20 µM, 200 µl) and stood the mixed solution still at 4° C. for 1 hour. The observed value of the resulting composite by ESI-TOF MS was 17808.0, which well agreed with the calculated value 17809.1 of the composite of cod-free Rh(I)(dppe) and apo-H64D Mb.

Example 7

Hydrogenation Reaction of Olefin 1

The rhodium complex-apomyoglobin composite Rh(dppe).apo-H64A Mb obtained in Example 3 was used for hydrogenation reaction of acrylic acid. The concentration of Rh of the purified composite was determined by atomic absorption spectroscopy. Acrylic acid went through a hydrogenation reaction in 50 mM phosphate buffer (pD 7.0) for 5 hours under the conditions of [Rh]/[substrate]=1/100, a temperature of 35° C., and a hydrogen pressure of 5 atm. Here pD represents $-\log_{10}[D+]$ (D is deuterium). The procedure placed an aqueous solution of the rhodium complex-apomyoglobin composite (0.5 mM, 1 ml, 0.5 µmol) in an auto clave, added an aqueous solution of acrylic acid (50 mM, 1 ml, 50 µmol) to the aqueous solution of the rhodium complex-apomyoglobin composite, and replaced the atmosphere in the auto clave with gaseous hydrogen for the hydrogenation reaction under the above conditions. This hydrogenation reaction changed acrylic acid to propionic acid. The turnover number measured by $^1$H-NMR was 0.68 h$^{-1}$.

Example 8

Hydrogenation Reaction of Olefin 2

Acrylamide was subjected to hydrogenation reaction with the rhodium complex-apomyoglobin composite Rh(dppe).apo-Mb obtained in Example 4, according to the same procedure as that of Example 7. This hydrogenation reaction changed acrylamide to propionamide. The turnover number measured by $^1$H-NMR was 0.60 h$^{-1.}$ Example 9

Various metal complex-protein composites were synthesized according to reaction formulae shown in FIGS. 2(a) through 2(d). Apomyoglobin used here was apo-H64D Mb. The observed values of the resulting metal complex-protein composites by ESI-TOF MS were also shown in FIG. 2. Concrete procedures of the syntheses were discussed below.

FIG. 2(a): The procedure of the synthesis mixed an apo-H64D solution (212 µM, 14 ml) with an acetone solution of [Rh(cod)Cl]$_2$ (10 mM, 150 µl) and stood the mixed solution still at 4° C. for 10 minutes. The mixed solution was dialyzed overnight with 10 mM Bis Tris/HCl buffer solution (pH 6.0). The reconstructed rhodium complex-apomyoglobin composite Rh(cod).apo-H64D Mb was purified by gel filtration with G25 and G50. The observed value of the composite by ESI-TOF MS was 17516.6, which well agreed with the calculated value 17519.1.

FIG. 2(b): A palladium complex-apomyoglobin composite Pd(dppe)-apo-H64D Mb was obtained according to the same procedure as that of FIG. 2(a), except that a Pd(dppe) DMF solution prepared by mixing Pd(dppe)Cl$_2$ and AgBF$_4$ in DMF and liberating Cl was used as the metal complex solution. The observed value of the composite by ESI-TOF MS was 17814.8, which well agreed with the calculated value 17812.0.

FIG. 2(c): A methanol solution of dichloro(p-cymene) ruthenium dimmer (2 equivalent weight) was added to a 5 mM ammonium acetate solution of apo-H64D Mb (20 µM, 200 µl), and the mixed solution was stood still at 4° C. for 1 hour. The observed value of the composite by ESI-TOF MS was 17544.3, which well agreed with the calculated value 17543.4.

FIG. 2(d): A ruthenium complex-apomyoglobin composite was obtained according to the same procedure as that of FIG. 2(c), except that a mixture of a methanol solution of dichloro(p-cymene)ruthenium dimmer (10 mM, 100 µl) and a methanol solution of 1,8-diaminonaphthalene (20 mM, 100 µl) mixed at room temperature, stirred for 1 minute, and stood still overnight at room temperature was used as the metal complex solution. The observed value of the composite by ESI-TOF MS was 17700.9, which well agreed with the calculated value 17699.6.

A composite of apocytochrome c was discussed as another example. The procedure mixed apocytochrome c with ruthenium chloride (p-cymene)(4-methyl-1,2-benzenediamine) at a rate of 1 to 1 or 1 to 2 and placed the mixture on ice for more than 10 minutes. The mixture was dialyzed with ammonium acetate buffer (5 mM, pH 6.8, 4° C.) for 12 hours and was passed through a G50 gel filtration column equilibrated by ammonium acetate buffer (5 mM, pH 6.8 4° C.) for purification. This gave a ruthenium (p-cymene)(4-methyl-1,2-benzenediamine)-apocytochrome c composite. The observed value of the composite by ESI-TOF MS was 12097.1, which well agreed with the calculated value 12098.

What is claimed is:

1. A metal complex-protein composite, comprising an apoprotein having a cavity and a metal complex, wherein the apoprotein is selected from the group consisting of apomyoglobin, apohemoglobin, apoheme oxygenase, apocatalase, apoferritin, and their variants;
   the metal complex is prepared by complexation of a metal ion with a ligand;
   the metal ion is selected from the group consisting of rhodium, ruthenium, and palladium;
   the metal complex-protein composite has a structure such that the metal complex is received in the cavity of the apoprotein;
   the metal complex is selected such that the metal complex does not cause degradation or instability of the apoprotein; and
   amino acid residues of the apoprotein coordinate with the metal complex.

2. The metal complex-protein composite of claim 1, wherein the apoprotein comprises an amino acid residue located in the cavity that forms a non-covalent bond to the ligand of the metal complex.

3. The metal complex-protein composite of claim 1, wherein the apoprotein having the cavity is obtained by removing a heme from a heme-containing protein.

4. The metal complex-protein composite of claim 1, wherein:
   the apoprotein is a variant of an apomyoglobin; and
   a histidine hydrogen bonded to oxygen and combined with iron in myoglobin is replaced in the variant.

5. The metal complex-protein composite of claim 1, wherein the metal ion is rhodium.

6. The metal complex-protein composite of claim 5, wherein the ligand is a compound having at least two diphenylphosphino groups.

7. The metal complex-protein composite of claim 5, wherein the the ligand is given by Formula (1):

$$R^1, R^2, P-J-PR^3R^4 \qquad (1)$$

where:
   $R^1$, $R^2$, $R^3$ and $R^4$ each independently represents a substituted hydrocarbon having 1 to 10 carbon atoms, a non-substituted hydrocarbons having 1 to 10 carbon atoms, a substituted phenyl or a non-substituted phenyl; and
   J represents a substituted hydrocarbon having 1 to 10 carbon atoms, a non-substituted hydrocarbon having 1 to 10 carbon atoms, or two adjacent carbon atoms in a benzene rings.

8. A hydrogenation catalyst, comprising the metal complex-protein composite of claim 1, the hydrogenation catalyst being capable of accelerating hydrogenation of an olefin in water.

* * * * *